United States Patent [19]

Iriguchi et al.

[11] 4,344,560
[45] Aug. 17, 1982

[54] CONTAINER, APPARATUS AND METHOD FOR SEPARATING PLATELETS

[75] Inventors: Norio Iriguchi, Fuji; Hiroshi Unno, Shizuoka; Nobuaki Tsuda, Fuji, all of Japan

[73] Assignee: Asahi Kasei Kogyo Kabushiki Kaisha, Osaka, Japan

[21] Appl. No.: 198,741

[22] Filed: Oct. 20, 1980

[30] Foreign Application Priority Data

Nov. 2, 1979 [JP] Japan .................... 54-141190
Sep. 10, 1980 [JP] Japan .................... 55-124674

[51] Int. Cl.³ .................... B04B 11/02; B04B 3/00
[52] U.S. Cl. .................... 233/19 A; 233/26;
210/96.1; 210/787; 210/927; 422/44; 23/913;
220/20.5
[58] Field of Search .......... 233/26, 27, 28, 19 R,
233/19 A; 210/782, 787, 96.1, 927; 220/20.5;
422/44; 23/913

[56] References Cited

U.S. PATENT DOCUMENTS

| | | | |
|---|---|---|---|
| 2,532,792 | 12/1950 | Svensjo | 233/19 A |
| 3,679,128 | 7/1972 | Unger et al. | 233/27 |
| 3,987,961 | 10/1976 | Sinn et al. | 233/19 R |
| 4,007,871 | 2/1977 | Jones et al. | 233/27 |
| 4,077,396 | 3/1978 | Wardlaw et al. | 210/927 X |
| 4,082,085 | 4/1978 | Wardlaw et al. | 210/927 X |
| 4,091,989 | 5/1978 | Schlutz | 233/27 X |
| 4,114,802 | 9/1978 | Brown | 233/26 |
| 4,284,602 | 8/1981 | Kelton et al. | 233/26 X |

Primary Examiner—Kenneth M. Schor
Attorney, Agent, or Firm—Sprung, Horn, Kramer & Woods

[57] ABSTRACT

A container for the continuous centrifugal separation of platelets component in blood, having a first and a second closed chambers adaptable to be rotated around a rotation axis. Whole blood is continuously introduced into the first chamber. Platelet-rich plasma being obtained as supernatant in the first chamber being discharged through a first outlet port opened at a relatively short distance from the rotation axis and being then introduced into the second chamber. Precipitation in the first chamber being discharged through a second outlet port opened at a relatively long distance from the rotation axis. The consistency of the blood in the first chamber being monitored at a predetermined position which differs from the opened position of the first outlet port and being located between the opened positions of the first and second outlet ports with respect to the distance from the rotation axis. The quantity of the discharge flow through at least one of the first and second outlet ports being controlled so that the consistency of blood maintain a certain constant value. Supernatant in the second chamber is discharged through a third outlet port opened to the second chamber. Platelets component in a high purity content is obtained as precipitation in the second chamber.

10 Claims, 20 Drawing Figures

CONTAINER, APPARATUS AND METHOD FOR SEPARATING PLATELETS

BACKGROUND OF THE INVENTION

This invention relates to a container, an apparatus and a method for continuously separating the platelets by applying centrifugal force to blood.

In recent years, blood taken out from human donors at blood centers or hospitals has often been separated into several blood components. A particular component is transfused to a patient who requires the component and another component is transfused to another patient who requires it. This is generally referred to as "component transfusion" as opposed to transfusing whole blood. Especially, platelets component is often transfused to a patient who has trouble with acute or chronic leukemia, cancer or infection or who is under a surgical operation, because the platelets adhere to the injured blood vessel wall and form an aggregation to prevent the blood from bleeding out.

In order to separate platelets component from blood in a relatively high degree of purity, a centrifugal force is applied to the blood at first to obtain platelet-rich plasma as supernatant, and then the platelet-rich plasma is further subjected to a centrifugal force so that the platelets component is separated. Such a method for the separation of platelets component is known, as disclosed in U.S. Pat. Nos. 4,010,894 and 4,146,172.

The process of continuously and hermetically treating blood, in which the blood is introduced into a processing chamber to which a centrifugal force is applied by rotating said chamber so that separated components, such as red blood cells, plasma and the other components, are discharged from the chamber, is important from the viewpoint of keeping the blood sterile and free from contaminents of the outside environment and also for using as small as possible amount of the blood taken out from donors at one time so that the risk like hypovolemia is reduced. It is also important to appropriately control the flow of the separated components, such as red blood cells, plasma and the other components, which are discharged from the processing chamber through pipes. Especially, the ratio of the quantities of the respective components must be precisely controlled. Unless such a control is appropriately effected, continuous separation would be almost impossible. According to a result of an experiment of the apparatus disclosed in the above-mentioned U.S. Pat. No. 4,010,894, it was confirmed that the continuous process was almost impossible. That is to say, some of the red blood cells which were precipitated in the first chamber without control were transferred to the second chamber.

According to a result of an experiment of the apparatus disclosed in the above-mentioned U.S. Pat. No. 4,146,172, it was confirmed the purity of platelets components obtained in the second chamber as the precipitate was about 92 percent, and the rest 6 percent was red blood cells and the rest 2 percent was white blood cells.

In addition, when experimenting with the apparatus disclosed in the above-mentioned U.S. Pat. No. 4,146,172, the inventors found that sometimes the blood flows backward. Blood is a suspension which consists of living cells, so that if a shearing force is exerted on the flow of the blood or if the blood flows backward, hemolysis or congelation of the blood can be caused.

SUMMARY OF THE INVENTION

Accordingly, an object of the present invention is to provide a technique, wherein it is possible to separate and obtain platelets component in a very high degree of purity which contain almost no red nor white blood cells.

Another object of the present invention is to provide a simple means to control the ratio of the discharge quantities of respective components, each separation ratio of which can vary from time to time, without disturbing the flow of the blood and the components thereof.

An aspect of the present invention is to provide a container for continuously separating platelets component in blood, comprising a first and a second closed chambers adaptable to be rotated around a rotation axis, means for introducing whole blood into said first chamber, a first outlet port opened to said first chamber at a relatively short distance from said rotation axis for discharging platelet-rich plasma obtained as supernatant in said first chamber, a second outlet port opened to said first chamber at a relatively long distance from said rotation axis for discharging precipitation in said first chamber, at least a part of means for monitoring the consistency of the blood in said first chamber at a predetermined position which differs form the opened position of said first outlet port and is located between the opened positions of said first and second outlet ports with respect to the distance from said rotation axis, means for connecting said first outlet port with said second chamber, and a third outlet port opened to said second chamber for discharging supernatant in said second chamber and for depositing platelets component being obtained as precipitation in said second chamber.

The volume of said first chamber should be 20 to 200 ml in practical use, and is preferably 40 to 100 ml. The volume of said second chamber is 40 to 400 ml in practical use, and is preferably 80 to 200 ml. The total volume of said first and second chambers is preferably not more than 500 ml.

The predetermined position at which the consistency of blood in said first chamber is monitored, is located between a position "5" and a position "95", assuming a scale of 100 provided between the opened position of said first outlet port (which is the position "100") and the opened position of said second outlet port (which is the position "0"). Under this condition, it is possible to obtain platelets component in a high purity level, so that the consistency thereof is from 99 to 99.9%, as will be described later.

When the predetermined position is located between the position "60" and the position "95", the number of platelet components being obtained per unit of time is large, as will be described later. That is to say, it was experimentally confirmed that the nearer to the opened position (position "100") of said first outlet port, said predetermined position is located from the position "5" to "95", the more platelet-rich plasma can be moved from said first chamber to said second chamber, as well as the more platelets component can be contained in the platelet-rich plasma.

The monitoring means comprises, for instance, a fourth outlet port opened to said first chamber at said predetermined position, and an optical sensor for detecting light transparency or reflection of the blood discharged through said fourth outlet port. Such an optical sensor comprising a photo-diode or a phototransistor is known in the prior art. Platelet-rich plasma has a relatively high light transparency, while red blood cells component has a poor light transparency but has a high light reflection to red ray.

The fourth outlet port may be connected to said whole blood introducing means so that the blood, after monitored of the consistency thereof, may be introduced again into said first chamber where it is centrifugally processed. In another case, the fourth outlet port may be connected to said second outlet port so that the blood, after the consisting thereof has been monitored, may be returned with the precipitation in the first chamber to the donor.

The monitoring means can be provided in the interior of said first chamber. In this case, the monitoring means preferably comprises optical fiber(s), one end of which is located at said predetermined position and the other end of which is connected to an optical sensor provided in said first chamber.

In order to establish fluid communication between the rotating blood containers and a stationary terminal, said containers may further comprise flexible blood tubes which are connected to at least one of said whole blood introducing means, said second and third outlet ports, extending outside of said first and second chambers. Said fourth outlet port may be also connected with a flexible blood tube extending outside of said first chamber. These flexible blood tubes are preferably installed in a cable which is flexible but is torsionless.

At least one of said first and second chambers is preferably made of a relatively soft material, such as vinyle chloride, polyulethan or the like, and is preferably fitted in a rigid shell rotatable around said rotation axis. The second chamber is preferably made of a flexible material so that platelets component, which tend to be omnipresent on the outer peripheral wall of the second chamber, can be dispersed by pushing said wall from the outside. In this connection, under the condition that platelets component is well dispersed in the second chamber, transfusion of the platelets components is effectively carried out.

At least one of the first and second chambers, especially the first chamber, is preferably constructed at least as part of an annular channel, whose central axis is said rotation axis, thereby a circumfluent blood flow is obtained and an effective separation is attained with relatively small rotational radius and with a decreased volume in the annular chamber. The annular chamber may be formed not only as a single circular-shaped channel, but also as a spiral-shaped channel. The spiral-shape makes the channel longer, although the radius is small.

Another aspect of the present invention is to provide an apparatus for continuously separating platelets component in blood comprising a container including a first and a second closed chambers adaptable to be rotated around a rotation axis, means for continuously introducing whole blood into said first chamber, a first outlet port opened to said first chamber at a relatively short distance from said rotation axis for discharging platelet-rich plasma being obtained as supernatant in said first chamber, a second outlet port opened to said first chamber at a relatively long distance from said rotation axis for discharging precipitation from said first chamber, means for connecting said first outlet port with said second chamber, and a third outlet port opened to said second chamber for discharging a supernatant in said second chamber and for depositing platelets component being obtained as precipitation in said second chamber; means for rotatably supporting said container; blood tubes connected to at least one of said whole blood introducing means, said second and third outlet ports, extending outside of said first and second chambers; means for monitoring the consistency of the blood in said first chamber at a predetermined position which differs from the opened position of said first outlet port and is located between the opened positions of said first and second outlet ports with respect to the distance from said rotation axis; and, a driving means for rotating said container around said rotation axis.

Preferably, said blood tubes are flexible tubes, which are connected at one end thereof to one side of said container along said rotation axis, intermediate portions of said tubes are taken a roundabout way to said container, the other ends of said tubes are connected to a stationary terminal along said rotation axis at the other side of said container, and said driving means to rotate said container and said intermediate portions of said tubes at the speed ratio of 2:1 around said rotation axis. A driving means, such as disclosed in U.S. Pat. No. 3,586,413, may be used for the purpose of the continuous blood separating apparatus mentioned above. If such a driving means is used, destruction of blood cells, hemolysis and/or aggregation of platelets component are prevented from occurring by virtue of using none of rotary seals for connecting the rotating container with a stationary terminal or pipelines.

At least one of said blood tubes may be preferably installed in a flexible cable which is torsionless, said cable is connected at one end thereof to one side of said container along said rotation axis, an intermediate portion of said cable is taken a roundabout way to said container and the other end of said cable is connected to a stationary terminal, so that by rotating said intermediate portion of the cable around said rotation axis, said container is rotated at two times the revolutional speed with respect to the revolutional speed of said intermediate portion of the cable, by virtue of the anti-torsibility of said flexible cable. A driving means, such as disclosed in U.S. Pat. No. 4,120,449, can be used for this purpose.

The cable should be preferably made of polyether-polyurethane, polyester-polyurethane, polyethylene, polypropylene, vinyle chloride, natural or synthetic rubber, or the like. The cable should be bendable in the longitudinal direction by human hands, that is, $EI < 10$ (kgcm$^2$), and more preferably it should be easily bent by using ones' fingers, that is, $EI < 1$ (kgcm$^2$). Here, E refers to the Young's modulus of the cable and I refers to the geometrical moment of inertia. The cable should be torsionless, that is $0.1$ (kgcm$^2$) $< GI_p$, and more preferably it should not be easily twisted by hands unless a very strong force is applied, that is, $1$ (kgcm$^2$) $< GI_p$. Here, G refers to the modulus of transverse elasticity of the cable and $I_p$ refers to the geometrical pole moment of inertia.

Still another aspect of the present invention is to provide a method for continuously separating platelets component in blood, comprising: introducing whole blood into a first closed chamber; applying a centrifugal force to the blood in said first chamber by rotating said first chamber around a rotation axis; discharging supernatant and precipitation in said first chamber through a first and second outlet ports, respectively, opened to said first chamber; monitoring the consistency of the blood in said first chamber at a predetermined position which differs from the opened position of said first outlet port and is located between the opened positions of said first and second outlet ports with respect to the distance from said rotation axis; controlling the increase or decrease of the quantity of discharge flow in at least one of said first and second outlet ports so that said consistency of the blood corresponds to a predetermined value; introducing platelet-rich plasma obtained as the supernatant in said first chamber through said first outlet port into a second closed chamber; and, applying a centrifugal force to the platelet-rich plasma in said second chamber so as to obtain platelets component as precipitation in said second chamber.

The precipitation in said first chamber is substantially red blood cells, while the supernatant in said first chamber is substantially platelet-rich plasma. Therefore, said predetermined value can be defined as a predetermined hematocrit, which means a percentage of red blood cells in volume. Such a value may be optionally determined, such as 2%.

As the speed of deposition of red and white blood cells is larger at the initial time of separation, it is advantageous to discharge the deposited components before the process of separation reaches a saturated status. That is to say, in order to conduct a large amount of blood and to obtain blood plasma component in a short time, it is advantageous that the quantity of whole blood being introduced into said first chamber is large enough so that hematocrit of said precipitation discharged through said second outlet port is not more than 1.8 times, and more preferably is not more than 1.6 times, of hematocrit of the whole blood. If the introduction quantity of the whole blood is constant, it is advantageous that the volume of said first chamber and/or the centrifugal force applied to the whole blood be reduced.

BRIEF DESCRIPTION OF THE DRAWINGS

The present invention may be more fully understood from the description set forth below of preferred embodiments of the invention, together with the accompanying drawings, wherein.

EXPLANATION OF PREFERRED EMBODIMENTS

Figure 1:
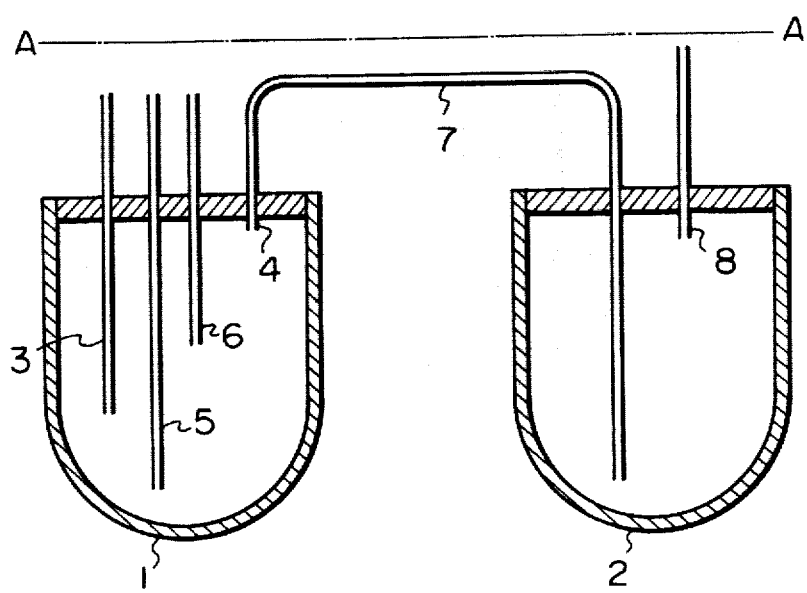
FIG. 1 is a schematic view illustrating the fundamental feature of a blood processing container of the present invention.

Through the several drawings, the same or corresponding parts, members or positions are designated identical to the reference numerals or marks.

Referring now to FIG. 1, a continuous blood processing container of the present invention is adaptable to be rotated around an axis A—A and to separate platelets component by applying a centrifugal force to the blood contained therein. The container comprises a first and a second blood processing closed chambers 1 and 2. A tube 3 serves to introduce whole blood to the first chamber 1. A first outlet port or discharge passage 4 is opened to the first chamber 1 at a position which is located at a relatively short distance from the rotation axis A—A and discharges supernatant component, that is, platelet-rich plasma. The other end of the passage 4 is elongated to the second chamber 2 through a tube means 7 which is opened to the second chamber at a position which is located at a relatively long distance from the rotation axis A—A. A second outlet port or discharge passage 5 is opened to the first chamber 1 at a position which is located at a relatively long distance from the axis A—A and discharges precipitation component. A third outlet port or passage 8 is opened to the second chamber 2 at a position which is located at a relatively short distance from the axis A—A. A fourth discharge passage 6, opened to the first chamber 1 at a predetermined position which differs from the opened position of the first passage 4 and is located between the opened positions of the first and second outlet ports 4 and 5 with respect to the distance from the rotation axis A—A, serves to discharge the blood for continuously monitoring the consistency of the supernatant and/or precipitation components at said predetermined position.

Figure 2:
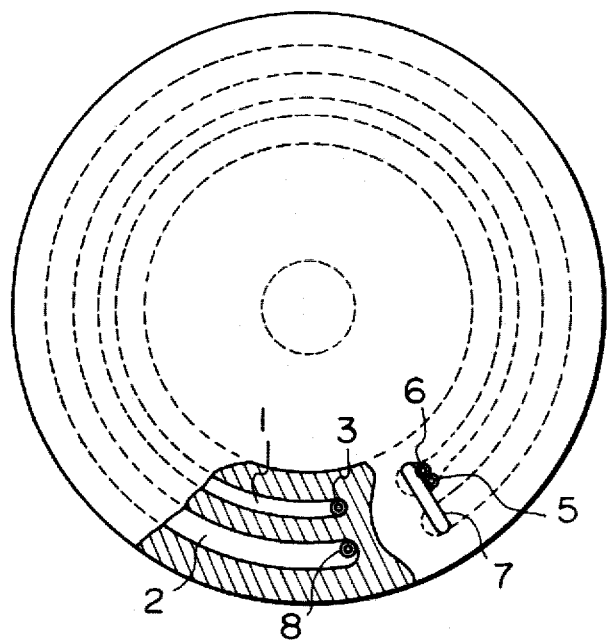
FIG. 2 is a plane view illustrating an embodiment of a blood processing container of the present invention.
Figure 3:
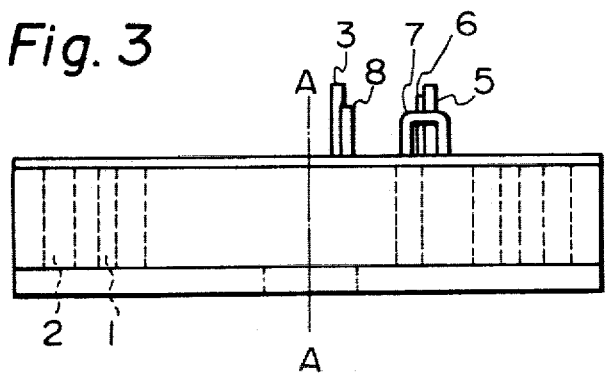
FIG. 3 is a front view of the blood processing container shown in FIG. 2.

Referring to FIGS. 2 and 3, the first and second chambers 1 and 2 are constructed as annular channels rotatable around their common central rotation axis A—A so that blood therein flows annularly through the circumferential passages. The width of the annular chambers is preferably 2 mm to 10 mm, as will be described later.

Figure 4:
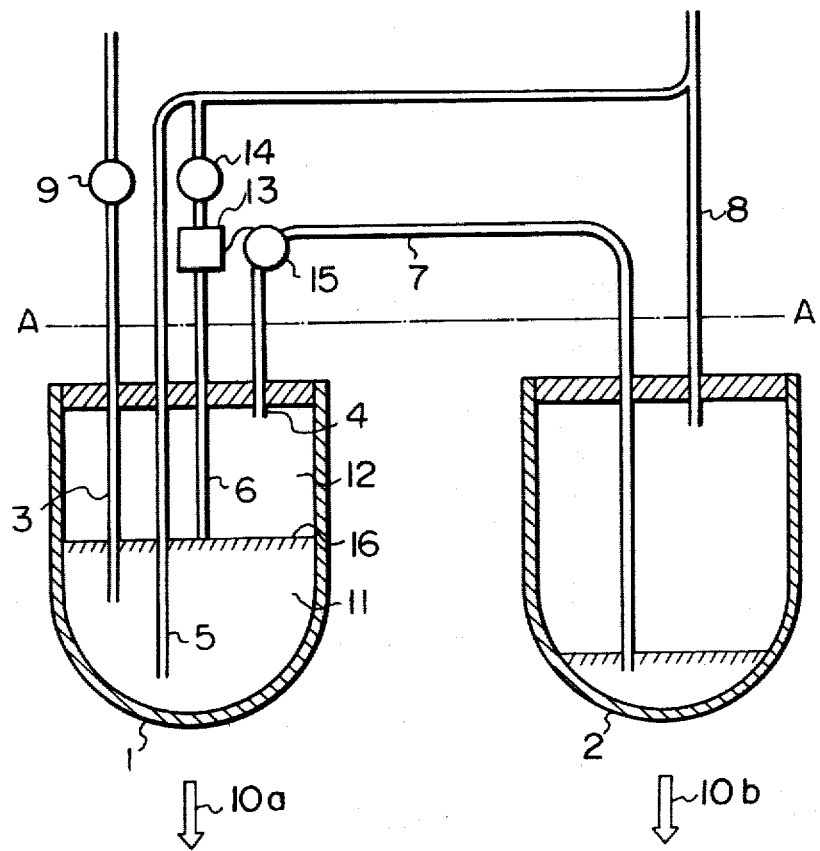
FIG. 4 is a schematic view illustrating the fundamental feature of another embodiment of a blood processing container of the present invention.

Referring to FIG. 4, whole blood is continuously introduced into the first processing chamber 1 rotating around the axis A—A through the introduction tube 3 which is provided with a pump 9 for this purpose. The first chamber 1 is subjected to a centrifugal force in the direction shown by an arrow 10a. Precipitation component 11 is discharged through the passage 5. The discharge passage 6 is a part of a means for monitoring the consistency of the supernatant and/or precipitation components and is provided with an optical sensor 13 and a pump 14. Supernatant component 12 is platelet-rich plasma which is introduced from the discharge passage 4 through the connection means 7 into the second processing chamber 2. The connection means 7 is provided with a pump 15. The optical sensor 13 serves to control the quantity of fluid flowing through the pump 15 so that said consistency of the blood maintains a predetermined constant value. Therefore, there always exists a boundary surface 16 between the precipitation and supernatant components 11 and 12 at the opened position of the discharge passage 6. Although the boundary surface 16 would be essentially moved in accordance with the change of the hematocrit of the whole blood being introduced and the inadequate ratio between the discharge quantities through the pipe 4 and pipe 5, the optical sensor 13 always actuates the pump 15 to control said ratio of discharge quantities so that the boundary surface 16 is controlled so as not to be moved. That is to say, if the boundary surface 16 moves in the centrifugal direction, that is, downward in FIG. 4, the optical sensor 13 controls to start the pump 15 or to increase the discharge quantity thereby, while if the boundary surface 16 moves upward in FIG. 4, the optical sensor 13 controls to stop the pump 15 or to decrease the discharge quantity thereby, so that the boundary surface 16 is always maintained at the predetermined constant position. Such a pump 15 can be also provided for the discharge pipe 5. In this case, contrary to the above, if the boundary surface 16 moves downward in FIG. 4, the pump 15 is stopped or the discharge quantity thereby is decreased, while if the boundary surface 16 moves upwardly in FIG. 4, the pump 15 is started or the discharge quantity thereby is increased. The platelet-rich plasma, introduced to the second chamber 2, is subjected to a centrifugal force in the direction shown by an arrow 10b, whereby platelets component is deposited and supernatant platelet-poor plasma is discharged to the outside through a discharge passage 8. Unless the product of the time during which the platelet-rich plasma stays and the centrifugal force in the chamber 2 is larger than the product of the time during which blood stays and the centrifugal force in the chamber 1, an effective deposition of platelet components would not be attained in the chamber 2. Consequently, it is necessary that the former be at least three times or desirably five times of the latter. The blood, monitored and passed through the passage 6, is joined with the precipitation discharged through the pipe 5 and the platelet-poor plasma discharged through the passage 8, and may be returned to the donors.

Figure 5:
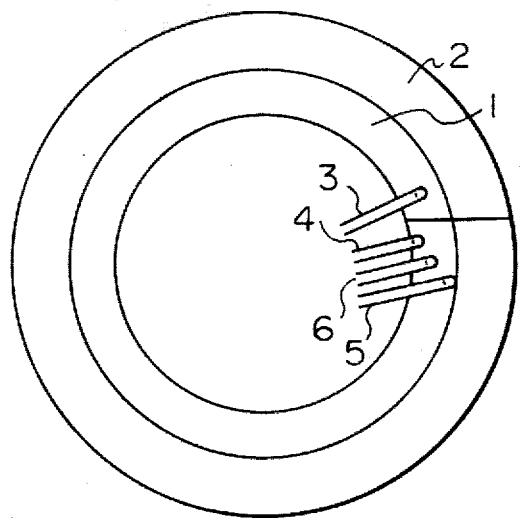
FIG. 5 is a schematic view for explaining a function of a blood processing container of the present invention.

In FIG. 5, the processing chamber 1 is an annular flow passage and has a volume of 75 ml, an inner diameter of 110 mm and an outer diameter of 126 mm. Inventors made an experiment using such a blood container. The container was rotated at 2000 RPM. Whole blood, the hematoric of which was 38% and in which $2.3 \times 10^8$ per ml platelets component was contained, was introduced through the tube 3 at a flow ratio of 40 ml/min. The supernatant, that is, platelet-rich plasma was discharge through the passage 4 and the precipitation was discharged through the passage 5. The precipitation was a suspension of platelet-rich plasma containing red blood cells and white blood cells in somewhat thick. The boundary surface 16, at which the pipe 6 is opened, was selected in various positions, and the quantity (ml/min.) of the platelet-rich plasma discharged through the passage 4 and the number (number/ml) of platelets component contained in the platelet-rich plasma were measured. The quantity of the sampled blood discharged through the passage 6 was always 1 ml/min.

Figure 6:
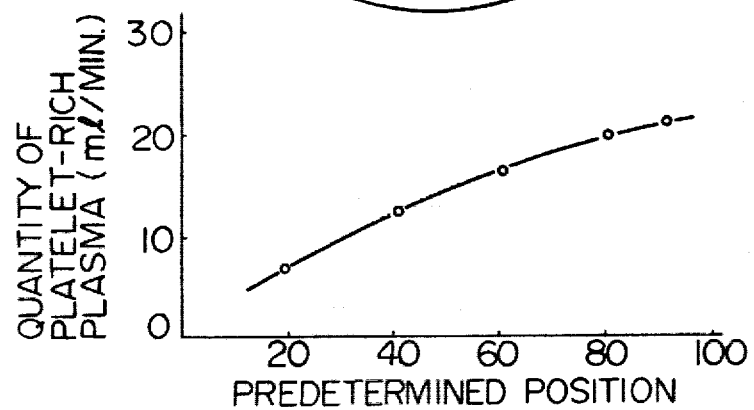
FIG. 6 is a diagram for illustrating an example of variation of the quantity of platelet-rich plasma moving from a first chamber to a second chamber according to the present invention.
Figure 7:
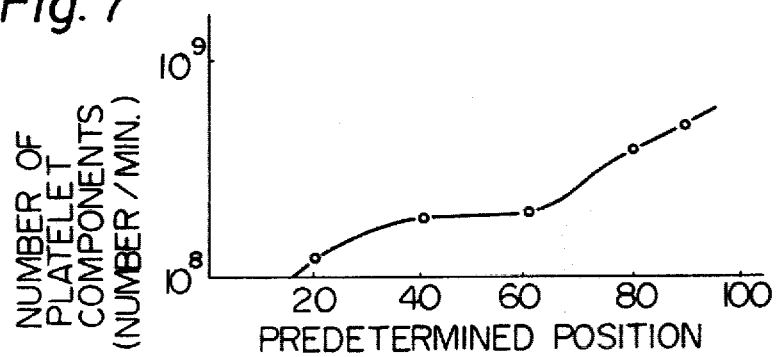
FIG. 7 is a diagram for illustrating an example of the variation of the number of platelets component being contained in platelet-rich plasma moving from a first chamber to a second chamber according to the present invention.

FIGS. 6 and 7 illustrate results of the experiment mentioned above. Although the quantity of the platelet-rich plasma was changed in accordance with the change of the discharged quantity by the pump 15, the mean quantity of the former is shown in these diagrams. It is assumed that, with respect to the rotation axis A—A, the opened position of the passage 4 is "100" and the opened position of the passage 5 is "0", and a divisional scale of 100 is provided therebetween. The nearer to "100", in other words, the nearer to the opened position of passage 4 the predetermined position was located, the larger the discharge quantity of the platelet-rich plasma became and the more the number of platelets per a unit volume was obtained. In order to increase the number of platelets transferred from the first chamber 1 to the second chamber 2, the predetermined position should preferably be selected between the positions "60" and "95", and more preferably between the positions "70" and "95".

Figure 8:
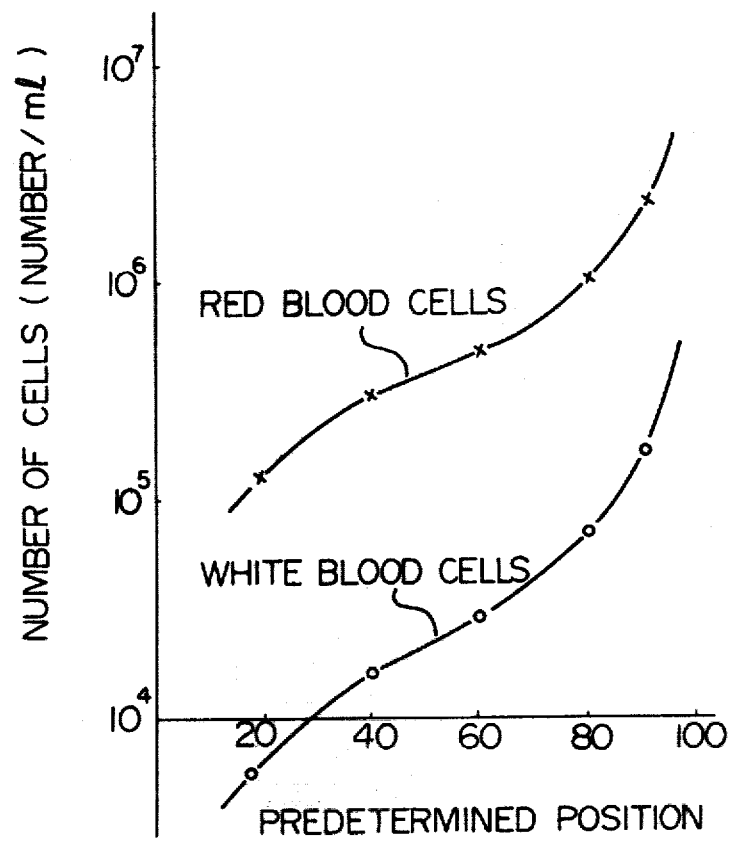
FIG. 8 is a diagram for illustrating an example of the variation of the number of red blood cells and white blood cells being contained in platelet-rich plasma moving from a first chamber to a second chamber according to the present invention.

As understood from FIGS. 7 and 8, in the platelet-rich plasma discharged through the passage 4, platelet of the order of $10^8$ (number/ml), red blood cells of the order of $10^5$ to $10^6$ (number/ml), and white blood cells of the order of $10^4$ to $10^5$ (number/ml) were obtained, so that the consistency of platelets component was 99 to 99.9%. If the predetermined position was selected between the positions "95" and "100", it is apparent in view of the abrupt change in FIG. 8 that the consistency would be sharply reduced.

Figure 9:
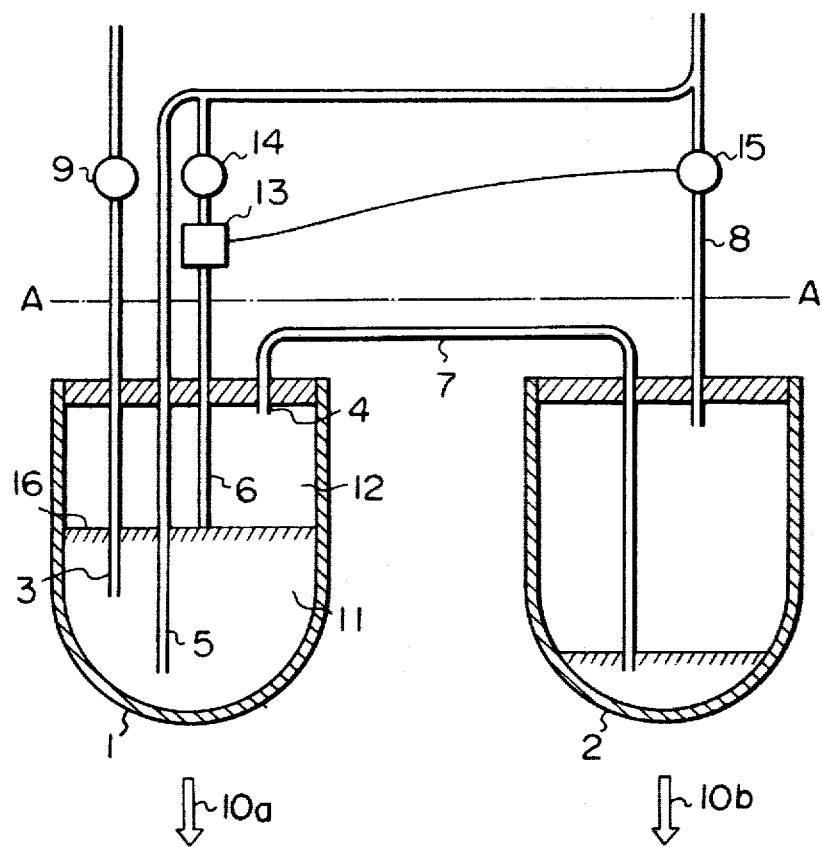
FIG. 9 is a schematic view illustrating the fundamental feature of a further embodiment of a blood processing container of the present invention.

In FIG. 9, the boundary surface 16 is selected at about position "70". The pump 15 is not provided for the connecting means 7, as shown in FIG. 4, but for the passage 8. The connecting means 7 is placed at the same side as the chambers 1 and 2 with respect to the rotation axis A—A and is rotated therewith. The number of passages which should be connected to the stationary outside pipelines is reduced to four, unlike to the container shown in FIG. 4 in which there are six passages. This is because the pump 15 is provided for the passage 8 by virtue of the closed chamber 2.

Figure 10:
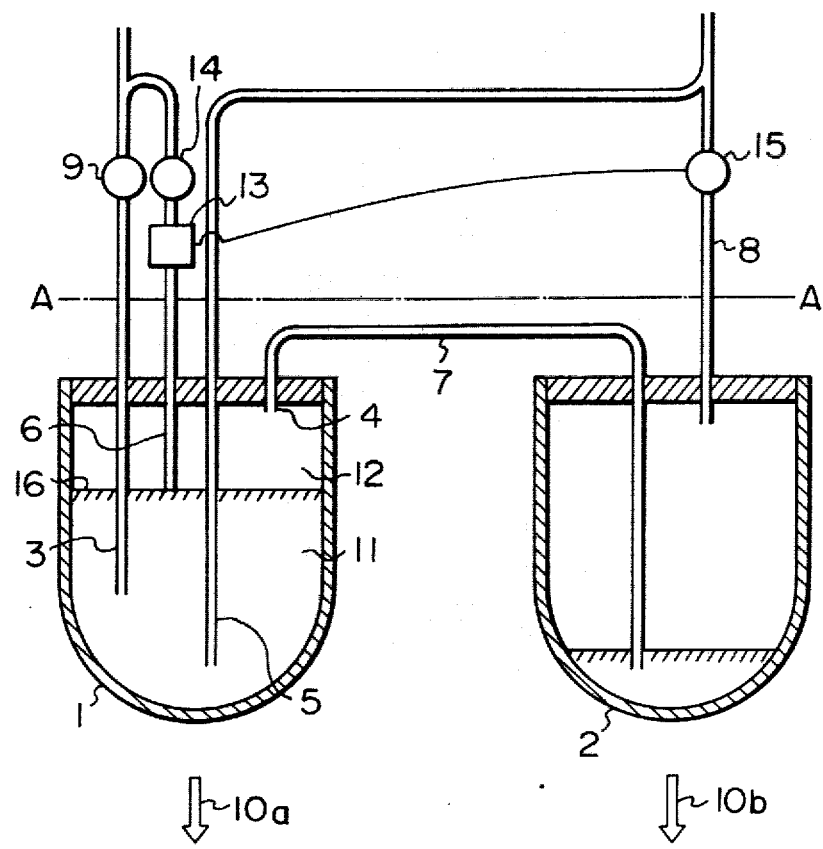
FIG. 10 is a schematic view illustrating the fundamental feature of a still further embodiment of a blood processing container of the present invention.

In FIG. 10, the passage 6 is connected with the optical sensor 13 and the pump 14 to the introduction tube 3, so that the monitored blood can be returned to the chamber 1 where it is centrifugally processed again.

Figure 11:
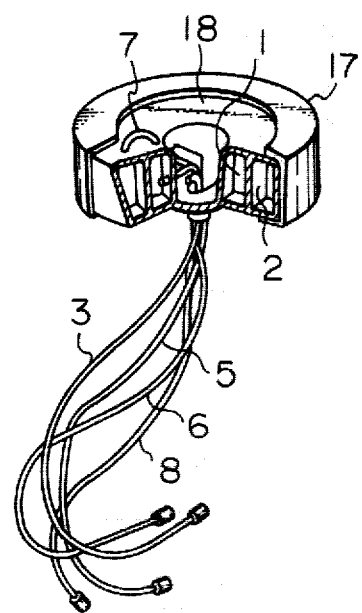
FIG. 11 is a perspective view of a blood processing container of the present invention.

In FIG. 11, the extensions of the introduction tube 3 and the discharge passages 5, 6 and 8 comprise respective flexible blood tubes. The chambers 1 and 2 are defined by an integral blood processing container 18 made of flexible resin, such as, vinyle chloride, which is received in a shell 17 made of aluminium and adaptable to be rotated. The rotary shell 17 can be made of relatively rigid material, such as polycarbonate or teflon. The flexible blood tubes can be made of vinyle chloride, silicone rubber, polyurethane or the like.

Figure 12:
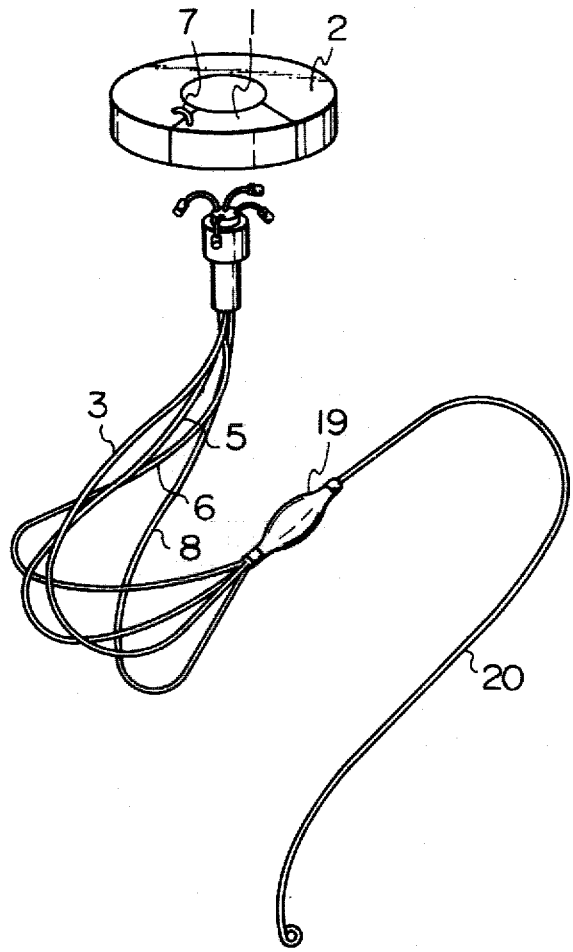
FIG. 12 is a perspective view of another embodiment of a blood processing container of the present invention.

In FIG. 12, the flexible tubes 3, 5, 6 and 8 can be separated from the chamber 1 or 2 at the one ends thereof and connected again thereto. The other ends thereof are connected to a covering means 19 which is provided with a flexible cable 20. Such a cable 20 is possible to receive the blood tubes 3, 5, 6 and 8 in a narrow passage thereof.

Figure 13:
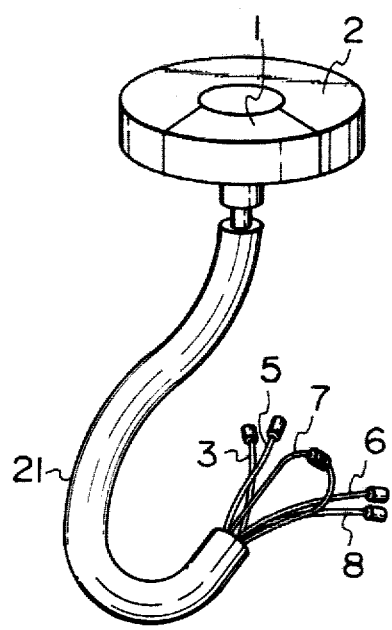
FIG. 13 is a perspective view of a further embodiment of a blood processing container of the present invention.

In FIG. 13, the extensions of the flexible blood tubes are received in a cable which can be easily bent but cannot be easily twisted, as mentioned before.

Figure 14:
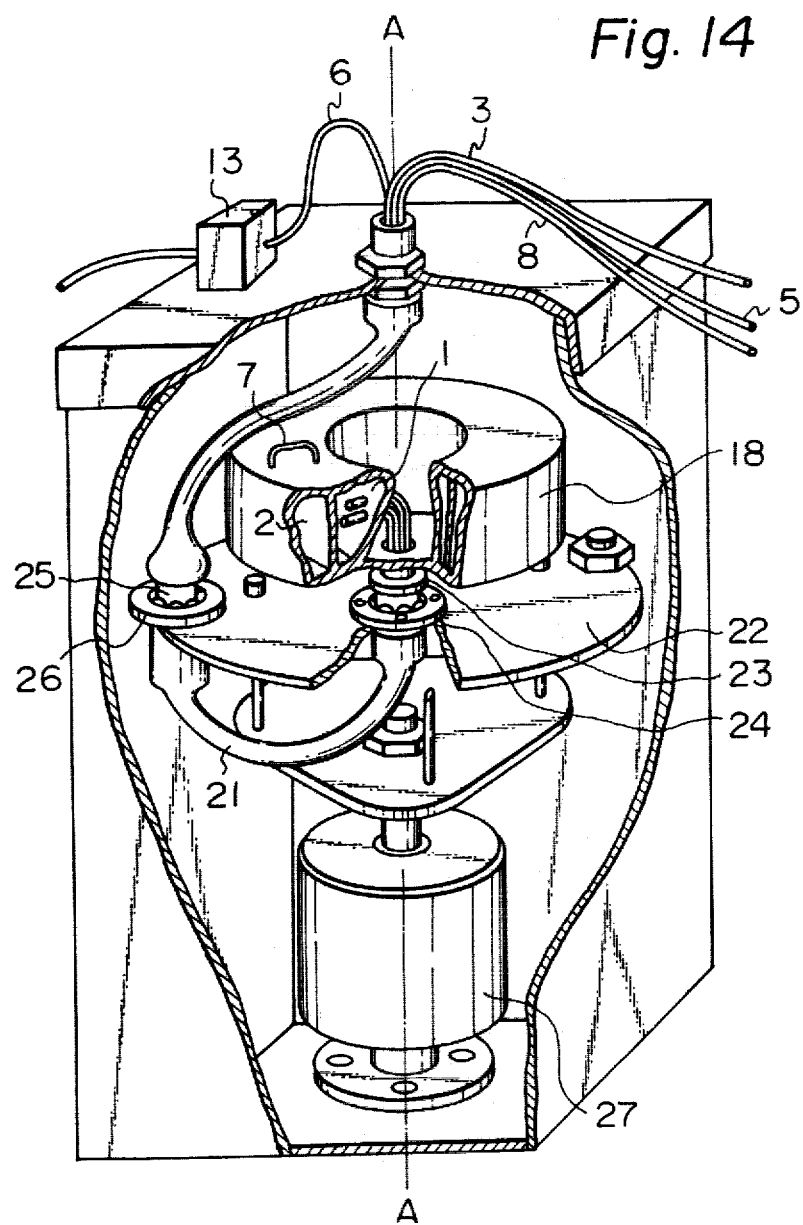
FIG. 14 is a perspective view illustrating a blood processing apparatus of the present invention, a part of which is not illustrated so as to show the interior.

Referring to FIG. 14, an apparatus of the present invention is shown, a part of which is taken away in order to illustrate the interior thereof.

The blood processing container 18 having chambers 1 and 2 is made of polycarbonate resin and is rotatable about the rotation axis A—A. A turntable 22 has, in order to rotatably support the container 18, a ball bearing 24 which is located on the axis A—A and carries a shaft 23 of the container 18. The blood tubes 3, 5, 6 and 8 are connected to the container 18 at one side thereof along the rotation axis A—A and are installed in a cable 21 which is easily bendable but not easily twistable. At the intermediate portion of the cable 21, which is taken a roundabout way with respect to the container is provided an aluminium pipe 25 which is rotatably supported by another ball bearing 26 of the turntable 22 located apart from the axis A—A. The other end of the cable 21 is connected to a stationary terminal at the other side of the container along the rotation axis A—A. When the turntable 22 is rotated around the rotation axis A—A by a motor 27, the blood processing container is rotated at two times the revolutional speed as compared with the turntable 22 due to the anti-torsibility function of the cable 21. In order to connect a rotating blood processing container to a stationary outside terminal or pipelines, a rotary seal may be used, such as is disclosed in "The Nature," Vol. 217, pages 816 through 818, and U.S. Pat. Nos. 3,489,145, 3,519,201 and 3,655,123. In addition, the means disclosed in the above-mentioned U.S. Pat. Nos. 3,586,413 and 4,113,173 can be used. In that case, one end of the flexible tubes 3, 5, 6 and 8 would be connected to the container at one side thereof and along the rotation aixs A—A, then the tubes would be taken a roundabout way to the container, and the other ends thereof would be connected to the stationary terminal along the rotation axis at the other side of the container. The container and the tubes would be rotated, respectively, around the common rotation axis at the speed ratio of 2:1.

Figure 15:
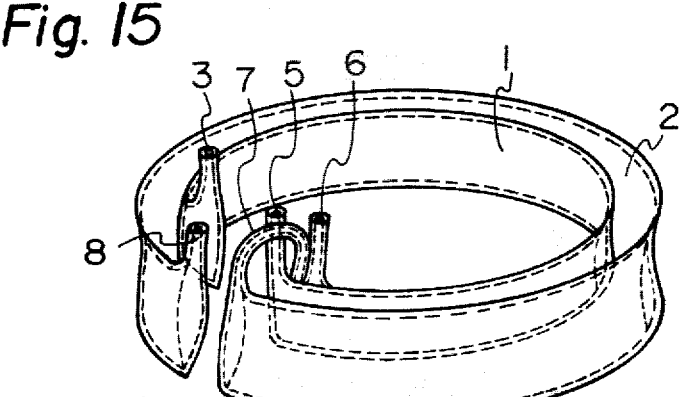
FIG. 15 is a perspective view of still further embodiment of a blood processing container of the present invention.
Figure 16:
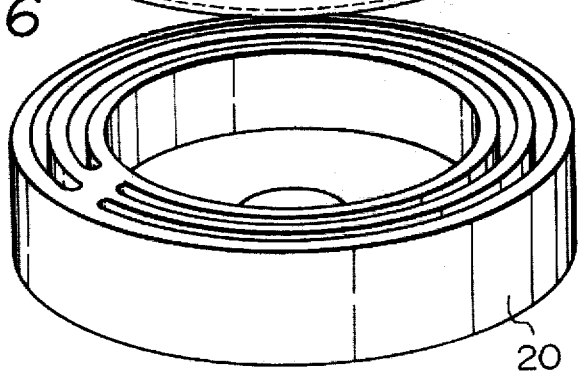
FIG. 16 is a perspective view of a shell adaptable to receive a blood processing container as shown in FIG. 15 and to rotate therewith.

In FIG. 15, the chambers 1 and 2 are made of vinyle chloride, sylicone rubber, polyulethane, polyethylene or like substances and form circumfluent blood flow channels. While, an aluminum shell 20, in FIG. 16, has two annular recesses in which the chambers 1 and 2 are inserted respectively. A cover member not shown may be detachably mounted on the shell 20 if necessary. The chambers 1 and 2 are in the form of flexible plain bags in which spacer members, which consist of, for instance, a plurality of projections, and do not disturb the flow of blood, may be provided for securing the necessary spaces therein. The width of the chamber 1 in the radial direction is relatively narrow, that is, from 2 mm to 8 mm, and is preferably from 2 mm to 6 mm, wherein it is confirmed that an effective separation of whole blood into precipitation and supernatant can be attained with a relatively small volume chamber 1 and a relatively small centrifugal force. This is because, the distance for deposition is small and the relatively heavy components, such as, red blood cells are smoothly and quickly deposited in a narrow and long channel.

Figure 17:
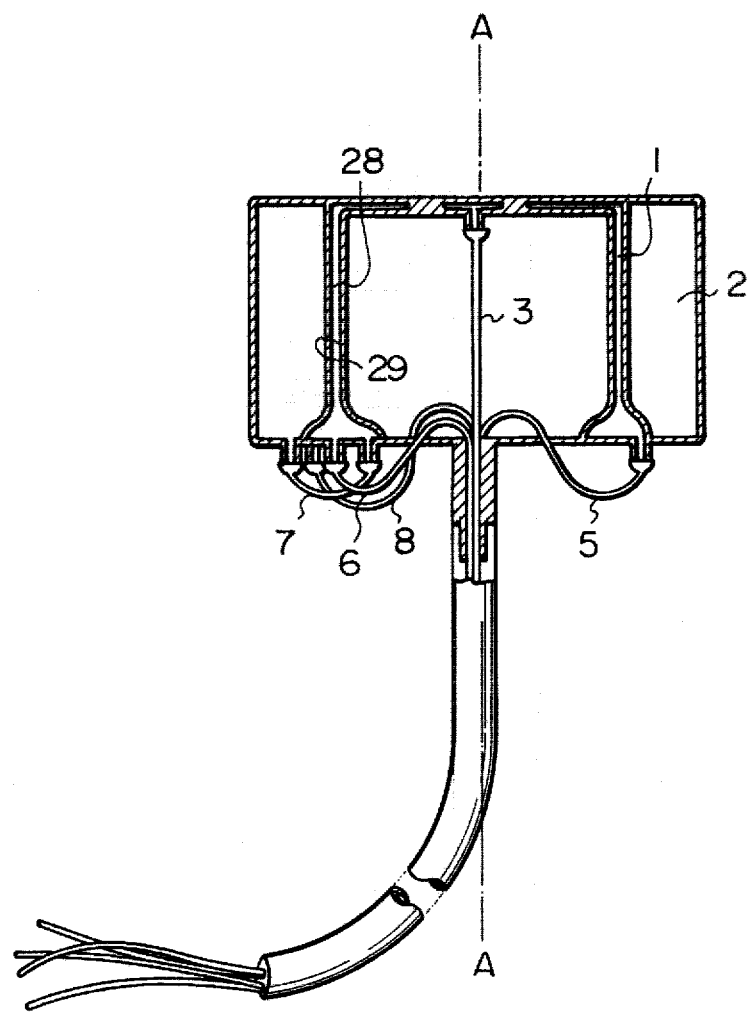
FIG. 17 is a front view of a still further embodiment of a blood processing container of the present invention.

In FIG. 17, the chamber 1 is defined between an outer wall 28 and inner wall 29 spaced at a relatively narrow distance therefrom, and constitutes a blood passage for allowing the blood to flow in the direction parallel to or substantially parallel to the rotation axis A—A, contrary to the embodiments described hereinbefore. The function of such a blood passage is disclosed in the above-mentioned "The Nature" Vol. 217, pages 816 through 818, and U.S. Pat. Nos. 3,489,145, 3,519,201 and 3,655,123. The blood container illustrated in FIG. 17 may be made of suitable flexible materials. In this case, however, the container should be covered by a rigid shell adaptable to the container. Between the outer wall 28 and the inner wall 29, spacer means which consists of, for instance, a plurality of projections, and do not disturb the flow of blood, may be provided for securing the necessary flow passage therebetween.

Figure 18:
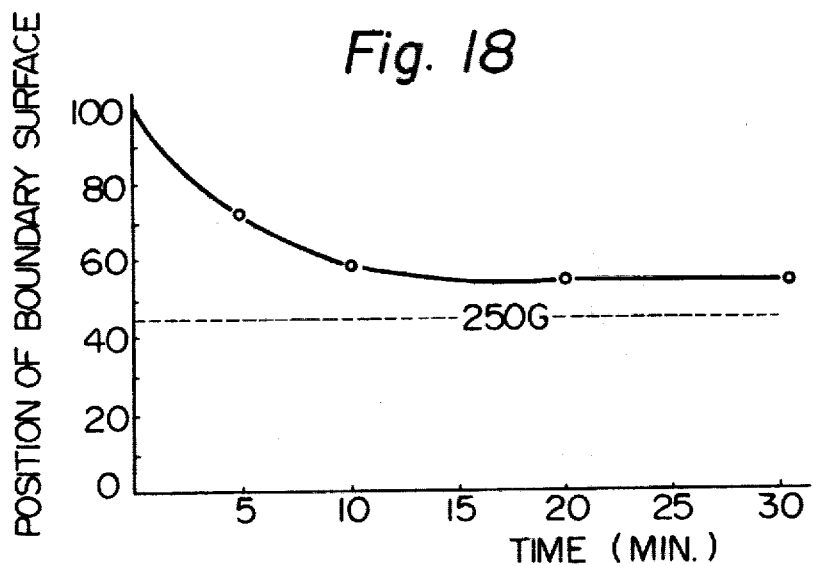
FIG. 18 is a diagram for illustrating an example of transition of the boundary surface between precipitation and supernatant when whole blood is subjected to a centrifugal force.
Figure 19:
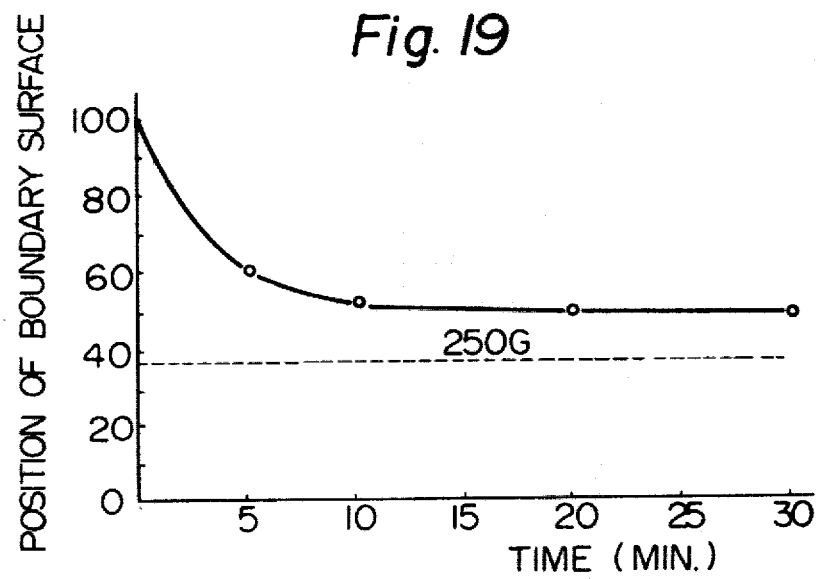
FIG. 19 is a diagram for illustrating another example of transition of the boundary surface between precipitation and supernatant when whole blood is subjected to a centrifugal force; and, FIG. 20 is a diagram for illustrating examples of quantities of precipitation and supernatant with respect to the quantity of whole blood being introduced into a first chamber.

FIGS. 18 and 19 illustrate results of an experiment, wherein the abscissa indicates the time and the ordinate indicates the position of the boundary surface between the precipitation 11 and the supernatant 12. In the ordinate, the point "0" is the opened position of the discharge passage 5 and the point "100" is the opened position of the discharge passage 6, as mentioned hereinbefore. In the experiment, whole blood having together with coagulants was subjected to a centrifugal force of 250 G (G; accelation of gravity.). Hematocrit of blood was 45% in FIG. 18 and 38% in FIG. 19. The boundary surface was selected as a position in which red blood cells were contained 2% of the blood. As will be understood from FIGS. 18 and 19, the boundary surface starts at the position "100" and reaches near the broken line after a long time. The change of the boundary surface is larger at the initial time of separation.

Hematocrit of whole blood of a healthy human is 35 to 50%. After such whole blood is subjected to a centrifugal force and at the time when the curves in FIGS. 18 and 19 reach near the broken lines, hematocrit of the precipitation becomes substantially 100%, which is two or two and a half times of the hematocrit of the initial whole blood.

Figure 20:
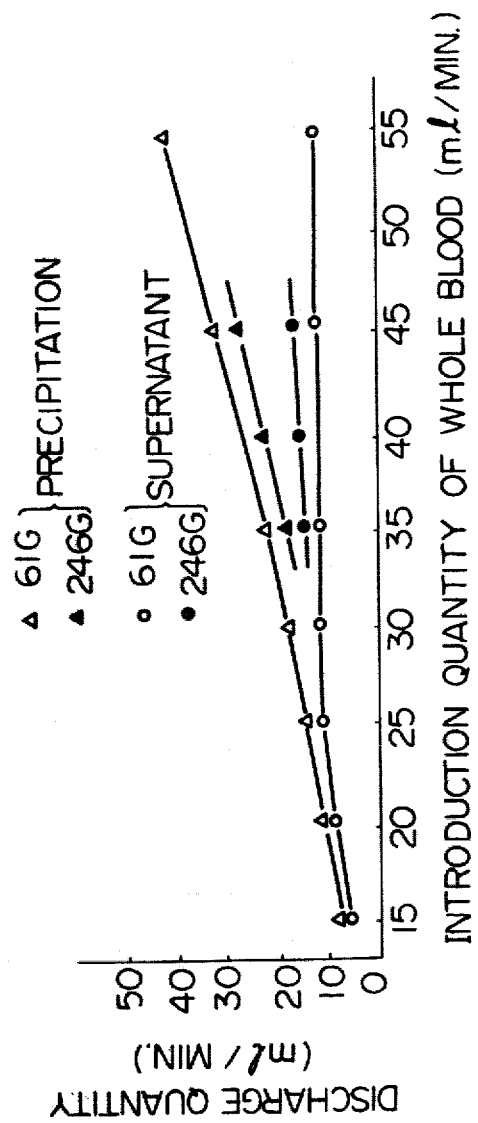

FIG. 20 illustrates results of an experiment, wherein a blood processing container, such as shown in FIG. 5, was used. The quantities of supernatant (platelet-rich plasma) discharged through the passage 4 and precipitation discharged through the passage 5 with respect to the quantity of whole blood being introduced into the chamber 1 were measured. 61C and 246C are the centrifugal accelerations at the opened position of the discharge passage 4. Where the introduction quantity of whole blood is large enough, such as not less than 25 ml/min, in case of 61C centrifugal acceleration, the quantity of the supernatent is almost unchanged even if the introduction quantity of whole blood is further increased, such as 40 ml/min. This means that where the introduction quantity of whole blood is large enough, the separated components are rapidly discharged before the process of separation reaches a saturated status. In this case almost all of white blood cells are discharged with the precipitation. The quantity of the whole blood which can be taken out from a human vein is usually 20 to 60 ml/min., so that the condition that the introduction quantity is not less than 25 ml/min., under 61C centrifugal acceleration, can be easily attained. Contrary to this, where the introduction quantity is small, such as 10 ml/min., the hematocrit of the precipitation becomes almost twice of the hematocrit of whole blood being introduced, and a layer of white blood cells is formed at the opened position of the discharge passage 6.

We claim:

1. A container for continuously separating platelets component in blood, comprising: a first closed chamber and a second closed chamber adaptable to be rotated around a rotation axis, means for continuously introducing whole blood into said first chamber, means defining a first outlet port opened to said first chamber at a relatively short distance from said rotation axis for discharging platelet-rich plasma being obtained as supernatant in said first chamber, means defining a second outlet port opened to said first chamber at a relatively long distance from said rotation axis for discharging precipitation in said first chamber, means for monitoring the consistency of the blood in said first chamber, said monitoring means containing a sensor means, with one end of the monitoring means being at a predetermined position which differs from the opened position of said first outlet port and which predetermined position is located between a position "60" and a position "95", assuming an equal divisional scale of 100 provided between the opened position of said first outlet port means, which is the position "100", and the opened position of said second outlet port means, which is the position "0", with respect to the distance from said rotation axis, means for connecting said first outlet port means with said second chamber, and means defining a third outlet port opened to said second chamber for discharging supernatant in said second chamber, whereby platelets component in blood are obtained as precipitation in said second chamber upon rotation of the second chamber around the rotation axis.

2. A container as set forth in claim 1, wherein said at least a part of monitoring means comprises means defining a fourth outlet port opened to said first chamber at said predetermined position.

3. A container as set forth in claim 2, said fourth outlet port means is, at the outside of said first chamber, in connection with one of said whole blood introducing means and said second outlet port means.

4. A container as set forth in claim 1, wherein said container further comprises blood tubes which are connected to at least one of said whole blood introducing means, said second outlet port means and third outlet port means, the blood tube extending outside of said first and second chambers.

5. A container as set forth in claim 2, wherein said container further comprises a blood tube which is connected to said fourth outlet port means, the blood tube extending outside of said first chamber.

6. A container as set forth in claim 4 or 5, wherein said blood tubes are flexible tubes.

7. A container as set forth in claim 6, wherein said flexible blood tubes are installed in a cable which is easily bendable but not easily twistable.

8. A container as set forth in claim 1, wherein said means for connecting said first outlet port means with said second chamber is a blood tube provided at the outside of and between said first and second chambers.

9. A container as set forth in claim 1, wherein at least one of said first and second chambers is made of relatively soft material and is received in a rigid shell rotatable around said rotation axis.

10. A container as set forth in claim 1, wherein one of said first and second chambers is at least a part of an annular chamber, whose central axis is said rotation axis and constitutes a channel for allowing blood to flow in the circumferential direction.

* * * * *